(12) United States Patent
Mizutani et al.

(10) Patent No.: US 7,549,980 B2
(45) Date of Patent: Jun. 23, 2009

(54) INTERLABIAL PAD

(75) Inventors: Satoshi Mizutani, Kanonji (JP); Koichi Yamaki, Kanonji (JP); Yuki Noda, Kanonji (JP); Megumi Tokumoto, Kanonji (JP); Akane Sakai, Kanonji (JP)

(73) Assignee: Uni-Charm Corporation, Ehime (JP)

( * ) Notice: Subject to any disclaimer, the term of this patent is extended or adjusted under 35 U.S.C. 154(b) by 325 days.

(21) Appl. No.: 10/705,811

(22) Filed: Nov. 10, 2003

(65) Prior Publication Data

US 2004/0147897 A1    Jul. 29, 2004

Related U.S. Application Data

(63) Continuation of application No. PCT/JP02/04889, filed on May 21, 2002.

(30) Foreign Application Priority Data

May 22, 2001    (JP)    ............... 2001-152403
Mar. 6, 2002    (JP)    ............... 2002-060070

(51) Int. Cl.
*A61F 13/15*    (2006.01)
*A61F 13/20*    (2006.01)
(52) U.S. Cl. ............... 604/385.17; 604/385.201
(58) Field of Classification Search ......... 604/385.201, 604/385.17
See application file for complete search history.

(56) References Cited

U.S. PATENT DOCUMENTS

| | | | |
|---|---|---|---|
| 4,595,392 A | 6/1986 | Johnson et al. | |
| 5,197,959 A * | 3/1993 | Buell | ............ 604/385.23 |
| D404,814 S | 1/1999 | Mayer | |
| 5,868,727 A | 2/1999 | Barr et al. | |
| 5,891,126 A * | 4/1999 | Osborn et al. | ............ 604/385.17 |
| 5,916,205 A | 6/1999 | Olson et al. | |
| 5,928,452 A | 7/1999 | McFall et al. | |

FOREIGN PATENT DOCUMENTS

| | | |
|---|---|---|
| EP | 0 136 524 A1 | 4/1985 |
| EP | 0 162 451 A1 | 11/1985 |
| EP | 888764 | 1/1999 |
| EP | 1 078 617 A2 | 2/2001 |
| FR | 2703244 | 10/1994 |
| JP | 49-3722 | 1/1974 |

(Continued)

OTHER PUBLICATIONS

Mizutani, et al., "Flap-Equipped Interlabial Pad", U.S. Appl. No. 10/705,670, filed Nov. 10, 2003.

(Continued)

*Primary Examiner*—Tatyana Zalukaeva
*Assistant Examiner*—Melanie J Hand
(74) *Attorney, Agent, or Firm*—Darby & Darby P.C.

(57) ABSTRACT

The present invention relates to an interlabial pad that is worn by female wearers, placed in intimate contact and supported between the labia, which provides an interlabial pad that causes no discomfort to the female wearer in the body motions of the wearer. The interlabial pad of the present invention is characterized by having bending elements which allows the interlabial pad to follow the changes in form flexibly even when a force is exerted on the interlabial pad by the wearer's body motion.

9 Claims, 11 Drawing Sheets

FOREIGN PATENT DOCUMENTS

| | | |
|---|---|---|
| JP | 54-168797 A1 | 11/1979 |
| JP | 54168797 | 11/1979 |
| JP | 60053144 | 3/1985 |
| JP | 61-108258 | 7/1986 |
| JP | 61149145 | 7/1986 |
| JP | 63260556 | 10/1988 |
| JP | 03-56366 | 3/1991 |
| JP | 05237151 | 9/1993 |
| JP | 05293138 | 11/1993 |
| JP | 06-506368 | 7/1994 |
| JP | 06/40203 | 10/1994 |
| JP | 08-215242 A1 | 8/1996 |
| JP | 2000-51267 | 2/2000 |
| JP | 2000501322 | 2/2000 |
| JP | 2001-507597 A1 | 6/2001 |
| JP | 2001-509402 | 7/2001 |
| JP | 2001522702 | 11/2001 |
| JP | 2002-513633 A1 | 5/2002 |
| JP | 2002-534163 | 10/2002 |
| TW | 247431 A1 | 5/1995 |
| TW | 294591 A1 | 1/1997 |
| TW | 338315 A1 | 8/1998 |
| TW | 386030 A1 | 4/2000 |
| TW | 386872 A1 | 4/2000 |
| TW | 394681 A1 | 6/2000 |
| TW | 416847 A1 | 1/2001 |
| TW | 442278 A1 | 6/2001 |
| TW | 450802 A1 | 8/2001 |
| TW | 454503 A1 | 9/2001 |
| TW | 470640 A1 | 1/2002 |
| TW | 524677 A1 | 3/2003 |
| WO | 92/11825 A1 | 7/1992 |
| WO | 9422405 | 10/1994 |
| WO | 95/00094 | 1/1995 |
| WO | 95/17148 A2 | 6/1995 |
| WO | 9602217 | 2/1996 |
| WO | WO-98/08475 A1 | 3/1998 |
| WO | WO-99/01096 A1 | 1/1999 |
| WO | WO-99/25290 A1 | 5/1999 |
| WO | WO-99/25295 A1 | 5/1999 |
| WO | 99/56681 | 11/1999 |
| WO | WO-99/55270 A1 | 11/1999 |
| WO | WO-99/55272 A1 | 11/1999 |
| WO | WO-99/56689 A1 | 11/1999 |
| WO | WO-00/19956 A1 | 4/2000 |
| WO | 00/40192 | 7/2000 |
| WO | 01/47458 | 7/2001 |

OTHER PUBLICATIONS

Mizutani, et al., "Interlabial Pad and Package Thereof", U.S. Appl. No. 10/705,810, filed Nov. 10, 2003.

Mizutani, et al., "Interlabial Pad", U.S. Appl. No. 10/705,406, filed Nov. 10, 2003.

Mizutani, Satoshi, "Interlabial Product Having Form for Finger Securement, and Individual Package", U.S. Appl. No. 10/705,779, filed Nov. 10, 2003.

Mizutani, et al., "Interlabial Pad", U.S. Appl. No. 10/705,408, filed Nov. 10, 2003.

Mizutani, et al., "Interlabial Pad Individual Packaging Vessel", U.S. Appl. No. 10/705,673, filed Nov. 10, 2003.

Mizutani, et al., "Interlabial Pad", U.S. Appl. No. 10/705,780, filed Nov. 10, 2003.

Mizutani, et al., "Interlabial Pad", U.S. Appl. No. 10/705,778, filed Nov. 10, 2003.

Mizutani, et al., "Interlabial Pad and Package Thereof", U.S. Appl. No. 10/705,404, filed Nov. 10, 2003.

Mizutani, et al., "Interlabial Pad and Package Thereof", U.S. Appl. No. 10/705,400, filed Nov. 10, 2003.

Mizutani, et al, "Interlabial Pad and Package", U.S. Appl. No. 10/706,303, filed Nov. 10, 2003.

Mizutani, et al., "Interlabial Pad Individual Packaging Body", U.S. Appl. No. 10/705,669, filed Nov. 10, 2003.

Mizutani, et al., "Interlabial Pad", U.S. Appl. No. 10/705,407, filed Nov. 10, 2003.

Mizutani, et al., "Interlabial Pad", U.S. Appl. No. 10/705,403, filed Nov. 10, 2003.

Mizutani, et al., "Interlabial Pad", U.S. Appl. No. 10/705,812, filed Nov. 10, 2003.

Mizutani, et al., "Individual Packaging Body and Outer Vessel Therefor", U.S. Appl. No. 10/705,402, filed Nov. 10, 2003.

Mizutani, et al., "Interlabial Pad", U.S. Appl. No. 10/705,399, filed Nov. 10, 2003.

Mizutani, et al., "Interlabial Pad Individual Packaging Vessel, and Individual Packaging Body", U.S. Appl. No. 10/705,781, filed Nov. 10, 2003.

* cited by examiner (A)

(B)

INTERLABIAL PAD

CROSS-REFERENCE TO RELATED APPLICATIONS

This application is a Continuation of International Application No. PCT/JP02/04889 filed May 21, 2002, which application published in Japanese on Nov. 28, 2002 as WO 02/094153 A1 under PCT Article 21(2).

BACKGROUND OF THE INVENTION

1. Technical Field

The present invention relates to an interlabial pad that is worn by female wearers, placed in intimate contact and supported between the labia.

2. Background Art

Conventionally, a sanitary napkin and a tampon are used generally as female sanitary products. Here, there have been great efforts made to prevent the leak of blood from gap caused by poor adhesion near the ostium vaginae as for the sanitary napkin. Moreover, as for the tampon, there have been great efforts made for relieving the foreign feeling and the discomfort when wearing the sanitary products as well as intervaginal wearing trouble due to the nature of those products.

Under such situation, sanitary products of the interlabial pad have attracted attention as a sanitary product positioned between the sanitary napkin and the tampon in recent years. The interlabial pad is used by inserting its portion between the labia and bringing into contact with the inner face of labia, it prevents the blood from leaking because of higher adhesion to the body than that of the sanitary napkin, and the blood from bringing widely into contact with the body by diffusing, so it is sanitary and clean. Moreover, the interlabial pad has characteristics that it excels in a feeling of wearing, is comfortable because of being smaller than the sanitary napkin, and has lower psychological resistance on wearing than that of the tampon which is inserted into the vagina.

Unlike sanitary napkins, which are fixed to the underwear or tampons, which are fixed by insertion into the vagina, the interlabial pad is usually used fixed to the body by inserting between the labia, which may make right and left phase shifts in body motions. Therefore, it is necessary that the interlabial pad can make right and left phase shifts flexibly to follow the wearers body motions. That is, it is required for the motions of the labia to correspond to the asymmetric body motions with respect to the body's longitudinal plane of symmetry, which extends along the anteroposterior axis, like putting one foot in front of the other alternately in walking. If the interlabial pad cannot follow the body motions and falls from the wearer's interlabial space, the resulting leak of blood is a significant problem.

An example of such device, thin comfortable interlabial absorbent structure (JP-A-2001-507597) is currently available. The interlabial absorbent structure comprises a pair of absorbent body panels that are sufficiently flexible so that the panels can, at least partially, conform to the walls of a wearer's interlabial space. The panels are joined by an isthmus which is positioned farthest into a wearer's interlabial space when the interlabial absorbent structure is worn. However, unlike usual sanitary napkins, the interlabial pad is not fixed to the underwear or fixed by insertion like tampons.

The interlabial absorbent structure is inserted into the interlabial space in such condition that the pad may slip or shift and is not fixed as securely as sanitary napkins or tampons. Therefore, with the wearer's body motion, slips between the interlabial absorbent structure (equivalent to the structure of the interiabial pad whose absorbent pad is joined by the isthmus) and the labia may tend to occur, which may make the wearer feel discomfort.

DISCLOSURE OF THE INVENTION

The present invention is directed to solve the problems pointed out above. The object of the present invention is, with the interlabial pad placed in intimate contact and supported between labia, to reduce as much as possible the discomfort which the wearer of the pad feels when some force is exerted on the interlabial pad and the inner walls of the labia by the body motions.

The inventors found out that it may be the slip between the interlabial pad and the inner walls of the labia or some force felt between the interlabial pad and the inner walls of the labia, even without any slips, that makes the wearer feel discomfort. Such force is apt to be produced by the wearer's asymmetric motions.

The innermost area of the interlabial space, that is, the vestibule floor can easily change in accordance with the wearer's (user's) motion. For example, when the wearer's weight is allocated downward (from the vestibule floor toward the end of the labia) with such motions as the wearer sitting down on a chair, the vestibule floor changes in form by being forced down. When the wearer's legs are moving back and forth alternatively in walking or other motions, the vestibule floor changes in form to flex, adjusting from right and left due to the pressure from the thighs.

With regard to the interlabial absorbent structure described above, the following has been found: The isthmus (equivalent to the top part of the folded pad), which is stiff as the isthmus is formed by joining the proximal edges of both absorbent panels, is placed facing the vestibule floor. Therefore, it is difficult for the isthmus to change its form to follow the changes in form of the vestibule floor described above, which may cause the wearer to sense the stiffness of the isthmus, that is, a feeling of discomfort with the wearer's body motions.

In view of the above, the inventors considered that if the part of the interlabial pad facing the vestibule floor follows the motions of the vestibule floor easily, the pad will not cause wearer discomfort, in addition, will also prevent leak of blood by avoiding creating a gap between the vestibule floor and the interlabial pad. That is, the following facts have been found: It is necessary to reduce a lengthwise stiffness of the interlabial pad for the interlabial pad product in a state. worn between the labia in order to cope with the changes in form of the vestibule floor by being forced down with such motions as the wearer sitting down on a chair. It is also necessary to reduce the breadthwise stiffness of the interlabial pad while worn between the labia in order to cope with the right and left changes in form of the vestibule floor in walking or other motions, due to the pressure from the thighs.

However, though the absorbent body, which is mainly responsible for maintaining the shape of the interlabial pad, is flexible, the capability of the absorbent body is limited as the absorbent body is relatively thick.

The present invention is developed based on the above-mentioned findings. The object of the present invention is to provide an interlabial pad which easily changes its form to follow the changes in form of the vestibule floor, in order to reduce the foreign feeling and further in order to prevent leak of blood. That is, an interlabial pad which has a shape to allow the pad to be easily inserted between the labia, consists of an absorbent body to absorb body fluid and a covering material to cover the absorbent body and is characterized by having at least one bending element in the absorbent body.

More specifically, the present invention offers the following:

(1) An interlabial pad with a size, weight, and flexibility capable of being held between labia by pinching a part or the whole portion of the interlabial pad naturally therebetween, having a direction of substantial parallel arrangement ("parallel direction") towards said labia and a direction of substantial vertical arrangement ("vertical direction"), further comprising, an absorbent body for absorbing body fluid and a coating material for enclosing said absorbent body, which defines a main form of said interlabial pad, wherein: said absorbent body includes one or a plurality of linear bending elements including a straight-line and a curved line form with a prescribed length and a prescribed width, which are provided in a prescribed position of said interlabial pad formed of a part with a smaller bending strength compared to parts other than said prescribed position.

The shape of the peripheral edge of the interlabial pad is not necessarily confined, as long as the shapes are suitable for fitting the labial area of the female wearers without difficulty. Examples of preferable shapes include elliptical shape, gourd shape and tear drop shape. "A part or the whole" above may mean that a part of the interlabial pad or the whole of the interlabial pad is inserted between the labia and becomes unseen. "Smoothly inserting" may mean to be inserted easily by the wearer of the interlabial pad by herself easily and "to hold" may mean that the pad does not fall off from the space where it is inserted. "Flexibility" may mean the adaptability in form which allows the pad to alter its form elastically when extrinsic forces such as external stress and pressure are exerted on the pad and which may include partial plastic changes in form. It is not necessary that the flexibility mean the local adaptability provided by the bending element described below but may mean general flexibility.

"Parallel direction" refers to a direction which is substantially parallel with the labia between which the interlabial pad is worn. As the direction coincides with the direction which is substantially parallel with the anteroposterior axis, the direction is determined by the direction in which the wearer wears the interlabial pad. That is, when a pad has a shape which is elongated longitudinally, the longitudinal axis is not necessarily parallel with the parallel direction but the direction in which the wearer wears the interlabial pad is the parallel direction. "Vertical direction" refers to a direction which is perpendicular to the parallel direction above and is included in a plane when the wearer stands upright wearing the pad. Consequently, it usually refers to longitudinal or lateral direction on the surface of the interlabial pad, which is flat. Bending strength may refer to a part which includes an area having lower bending element than that of the surrounding area. In addition, as bending is usually carried out along lines, bending element may also have a linear shape.

The interlabial pad (or absorbent body) may have any shape including a sheet, a cylinder, a sphere and a cube. With regard to these interlabial pads of various shapes, the directions (the parallel direction and the vertical direction) are also determined based on the wearer's position. Bending element may have a linear shape when projected a plane determined mainly by the parallel direction and the vertical direction (may refer to a horizontal plane for the wearer).

(2) The interlabial pad according to (1), wherein said bending element is formed of a bending element piece in which said part with a smaller bending strength is extended for a prescribed length, and said bending element piece is a "vertical bending element piece" being extended substantially parallel with said vertical direction.

Bending element piece may include parts whose bending strength (or bending resistance) is relatively low and may have a specified length. However, the bending strength of the bending element piece is not necessarily the same over all its length but may vary from part to part. Though the specified length can be determined in the individual case, it may usually be within the length or width of the absorbent body including the bending element piece.

(3) The interlabial pad according to (2), wherein said vertical bending element piece is arranged to cross a center line of said interlabial pad, which lies along said parallel direction of said interlabial pad.

The center line of the interlabial pad lying in the parallel direction of the interlabial pad refers to a line which extends substantially parallel in the "parallel direction", which is substantially parallel with the wearer's anteroposterior axis when the interlabial pad is worn, and at which the interlabial pad is divided into equal two parts. When the interlabial pad is symmetrical with respect to the wearer's anteroposterior axis, the center line coincides with the axis. If the interlabial pad is asymmetrical, the center line can be a line which divides the main part (notably, the absorbent body) into nearly symmetrical two parts. That is, to cross the center line, may mean to extend mainly to the right and left direction, being astride a part in proximity to the center line dividing the pad longitudinally into nearly equal parts ("central part"). However, unless specified, it is not necessary that the crossing is carried out parallel or nearly parallel with the right and left direction.

In such structure, on the center line along the parallel direction of the interlabial pad facing the vestibule floor, the bending elements extending in the vertical direction as crossing the center line along the parallel direction enables at least the absorbent body to change in form easily and lower the stiffness in both of the parallel direction and the vertical direction. This enables the pad to follow the changes in form of the vestibule floor more effectively, which reduces the foreign feeling caused by the wearer's body motions, in addition, makes the pad to contact the vestibule floor closer, which will prevent leak of blood.

(4) The interlabial pad according to any one of (1) to (3), wherein: said bending element is formed of a bending element piece in which said part with a smaller bending strength is extended for a prescribed length; and said absorbent body of said interlabial pad comprises a plurality of said bending element pieces being extended for a prescribed length in a state where said pieces are positioned substantially parallel with each other so that, when said absorbent body is extended flat, said plurality of bending element pieces appear to be in a staggered pattern.

Bending element piece above may mean a combination of straight lines, curved lines close to straight lines or curved lines. That is, it is not necessary that each of the plural bending element pieces has the same shape. However, in order to arrange each of the multiple bending element pieces to be substantially parallel, it is necessary that the shape of each bending element piece generally points in a certain direction, in which the main part of each bending element piece points. "When extending the absorbent body" means that the absorbent body may be used folded or bent because of its flexibility and it is better for objective identification of the shape of the absorbent body when extending the absorbent body along a surface. In such case, "appearing in a staggered pattern" may be considered that the bending element pieces are not in one line but in a staggered arrangement.

(5) The interlabial pad according to any one of (1) to (4), wherein: said bending element is formed of a bending element piece in which said part with a smaller bending strength is extended for a prescribed length; and a plurality of said bending element pieces are arranged to be in line as symmetry with respect to the center line of said interlabial pad, which lies along said parallel direction of said interlabial pad.

"Linear symmetry" may mean that the multiple bending element pieces are arranged symmetrically in right and left with respect to the center line of the interlabial pad.

(6) The interlabial pad according to any one of (1) to (5), wherein: said bending element is formed of a bending element piece in which said part with a smaller bending strength is extended for a prescribed length; and said bending element piece is a "parallel bending element piece" being extended substantially parallel with said parallel direction.

"Parallel bending element piece" may refer to a bending element piece which includes weak point of the bending strength and extends substantial parallel with the parallel direction.

(7) The interlabial pad according to any one of (1) to (6), wherein said parallel bending element piece is arranged near the center line of said interlabial pad, which lies along said parallel direction of said interlabial pad.

"The center line neighborhood" of the interlabial pad lying along the parallel direction of the interlabial pad may refer to the central part of the interlabial pad as described above.

(8) The interlabial pad according to any one of (1) to (7), wherein said bending element is formed of a bending element piece in which said part with a smaller bending strength is extended for a prescribed length, and said bending element piece is arranged to reach the peripheral edges of said absorbent body.

"The peripheral edge of the absorbent body" may refer to the part in the proximity to the edge of the absorbent body. This may mean, for example, when a bending element piece is formed by a slit, the slit should reach the edge of the absorbent body. Therefore, arrangement of bending element pieces, in the appropriate positions and directions, considering the length of the bending element pieces, will enable the bending element pieces to reach the peripheral edge.

(9) The interlabial pad according to any one of (1) to (8), wherein: said bending element is formed of a bending element piece in which said part with a smaller bending strength is extended for a prescribed length, and a first bending element piece extended for a prescribed length in substantially parallel with said vertical direction is positioned to cross the center line of said interlabial pad, which lies along said parallel direction; a second bending element piece extended for a prescribed length in substantially parallel with said parallel direction is positioned near the center line of said interlabial pad; and said first bending element piece and said second bending element piece cross each other near the center line of said interlabial pad.

For example, it may be considered the first bending element piece and the second bending element piece cross each other in the shape of a cross at center line neighborhood of the interlabial pad (central part).

(10) The interlabial pad according to any one of (1) to (9), wherein: said bending element is formed of a bending element piece in which said part with a smaller bending strength is extended for a prescribed length; and said bending element piece is positioned, in said vertical direction, in the halfway between the center part positioned near the center line of said interlabial pad and the peripheral edges of said interlabial pad, and extends for a prescribed length in substantially parallel with said parallel direction.

"Central part" may refer to the center line neighborhood of the interlabial pad, which extends substantially parallel in the parallel direction. "The peripheral edge of the interlabial pad" refers to an end (or an edge) of the interlabial pad. In this case, "the peripheral edge of the interlabial pad" may particularly refer to the right or left edge of the interlabial pad, that is, the right or left end of the vertical direction, which corresponds to the wearer's right and left directions. Therefore, "between the central part and the peripheral edge" may refer to a part which is located midway between the central part and the left (or right) edge of the interlabial pad and extends substantially parallel with the central part.

(11) The interlabial pad according to any one of (1) to (10), wherein said bending element is formed of a bending element piece in which said part with a smaller bending strength is extended for a prescribed length, the bending element is positioned near the center line of said interlabial pad, and extends in a V-shape towards the peripheral edges of said absorbent body from said vertical direction at a prescribed angle.

This bending element piece is nearly in the center of the interlabial pad and may be considered to be V-shaped. The V shape may follow the shape of the edge of the interlabial pad or may be reversed.

(12) The interlabial pad according to any one of (1) to (11), wherein said bending element is formed of a bending element piece in which said part with a smaller bending strength is extended for a prescribed length, and said bending element piece extends for a prescribed length at a prescribed angle between said parallel direction.

The above is a description of so-called slanted bending element pieces.

(13) The interlabial pad according to any one of (1) to (12), wherein said bending element is formed by a slit, a low-dense part, or a combination of these.

"The slit" may refer to a linearly extending space formed by removing the whole or a part of the filling material of the absorbent body in the absorbent body including the bending element piece. As the absorbent body is covered in the covering material, the absorbent body on both sides of the slit will not come loose. It may be considered that the absorbent body is bent along the crease formed by the covering material and the remaining filling material. Such slit can be made by stuffing a filling material which is separated in advance or by cutting the filling material by cutter or other tools. "Low density portion" may refer to a point where the density of the filling material of the absorbent body is low. Such part is usually easy to bend, and when bent, the point is crushed and consequently, the thickness of the absorbent body is actually reduced. "Compound of the slit and the low density portion" means that these means can be used being combined along the longitudinal direction of the bending element. In addition, these means can be used in combination in the same part. For example, a slit can be made in a low density portion by a cutter.

(14) The interlabial pad according to any one of (1) to (13), wherein: the opposite side surface to a body of said interlabial pad comprises a mini sheet piece which is provided over one side part to the other side part of both side parts with respect to the center axis substantially parallel with said substantially parallel direction of said interlabial pad; and a finger insert hole is formed between said mini sheet piece and said opposite side surface to the body.

"The opposite side surface to body" may refer to the surface opposite to the surface contacting the body or the outside of the back side sheet. "Central axis" may refer to an axis along the parallel direction which is defined above and the axis extending so that the axis will divide at least the main part of the interlabial pad into two nearly equal parts.

Therefore, "the side of both ends" may refer to the outer edges (or parts) of the interlabial pad away from the center line (corresponding to the direction in which the divided two parts of the interlabial pad spread from the center line as the center line divides at least the main part of the interlabial pad into two nearly equal parts).

Mini sheet piece is provided so as to stride from one side to the other side may mean that the mini sheet piece is attached to both edges of the above interlabial pad. "Finger insert hole" may refer to an open space surrounded by the ring or loop formed by the mini sheet piece and the opposite side surface to body.

(15) An interlabial pad according to any one of (1) to (14), wherein said interlabial pad is a pad for an incontinence of urine.

According to the interlabial pad of the present invention, the pad can be used for incontinence absorption pad. That is ostium vaginae where the blood is discharged and a pee hole where urine is discharged locate between labia, and the interlabial pad of the present invention to be used between labia can absorb urine also.

As described hereinbefore, the pad of the present invention can absorb urine around labia, especially around the pee hole and is useful for the absorbing pad for incontinence of urine, especially for a light incontinence of urine.

(16) An interlabial pad according to any one of (1) to (14), wherein said interlabial pad is a pad for absorbing vaginal discharge.

In accordance with the present invention, the interlabial pad can be used for the pad of absorbing the vaginal discharge. That is the interlabial pad is used between labia and can absorb the excretion other than the blood from ostium vaginae for the use therefore (for absorbing the vaginal discharge).

As described above, the pad can absorb the vaginal discharge in order to decrease the discomfort for the person, and is useful for the user who is not menstruating.

(17) A method of adjusting a form flexibility used for said interlabial pad with a size, weight, flexibility capable of being held between labia by a part or the whole portion of which being naturally inserted therebetween, having a direction of substantially parallel arrangement ("parallel direction") towards said labia and a direction of substantial vertical arrangement ("vertical direction"), further comprising: an absorbent body for absorbing liquid and a coating material for enclosing said absorbent body, which defines a main form of said interlabial pad; and one or a plurality of bending elements provided in a prescribed position of said interlabial pad with a smaller bending strength compared to a part other than said prescribed position, wherein the method comprises the step of: adjusting the form of said interlabial pad by a bending element application method using said bending element.

The method will make it easy to adjust the shape flexibility of the interlabial pad. If the wearer uses this method, the shape of the interlabial pad is easily adjusted.

(18) The method for adjusting a form flexibility according to (17), wherein said bending element application method comprises the step of changing the form, number, positioning area, and arrangement of said bending element.

The shape of the bending element may include the size, orientation and the like. "Arranged portion" refers to the point where the bending element is placed. "Arrangement" may mean how to arrange bending elements and can also be expressed as distribution.

BRIEF DESCRIPTION OF THE DRAWINGS

FIG. 3(A) is a front view of the interlabial pad which is used being folded. FIG. 3(B) is a side view of the pad seen from the left side.

FIG. 4(A) shows a cylindrical interlabial pad. FIG. 4(B) shows the interlabial pad being placed between the labia.

FIG. 5(A) shows a flat pad-type interlabial pad. FIG. 5(B) shows the interlabial pad being folded in use.

BEST MODE OF CARRYING OUT THE INVENTION

Next, the embodiments of the interlabial pad in the present invention will be described with reference to the figures.

[Basic Interlabial Pad]

Figure 1:
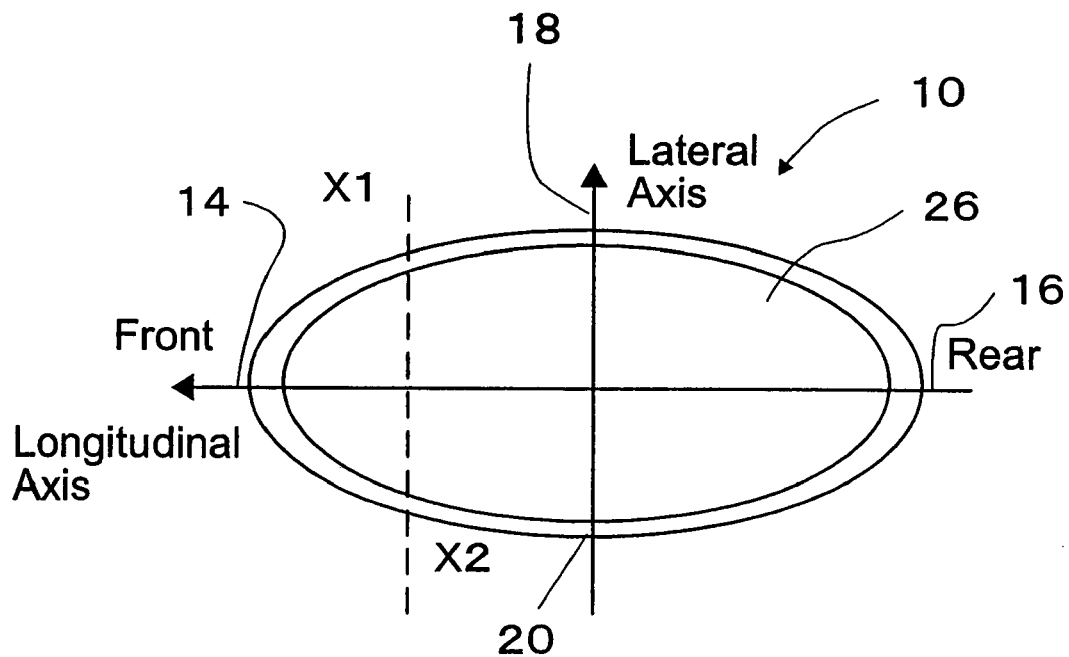
FIG. 1 is a plan view of an interlabial pad of the present embodiment seen from the body side surface.

FIG. 1 shows a schematic plan view of an interlabial pad 10. An interlabial pad of the embodiment essentially has a shape which is elongated longitudinally, that is, an elliptical shape having the major axis of front 14 to rear 16 on the longitudinal axis (X-axis), and the minor axis of right 18 to left 20 on the lateral axis (Y-axis). However, the shape of the product is not necessarily confined, as long as the shapes are suitable for the labial area and allow right and left phase shifts during use, such as elliptical shape, gourd shape and tear drop shape.

Figure 2:
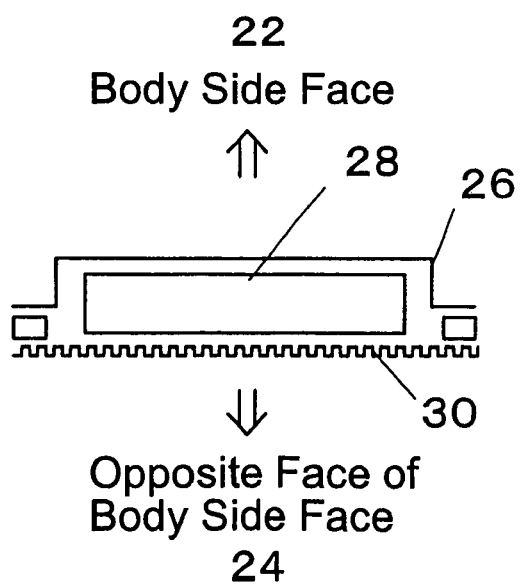
FIG. 2 is a cross-sectional view taken along line X1-X2 of FIG. 1.
Figure 3:
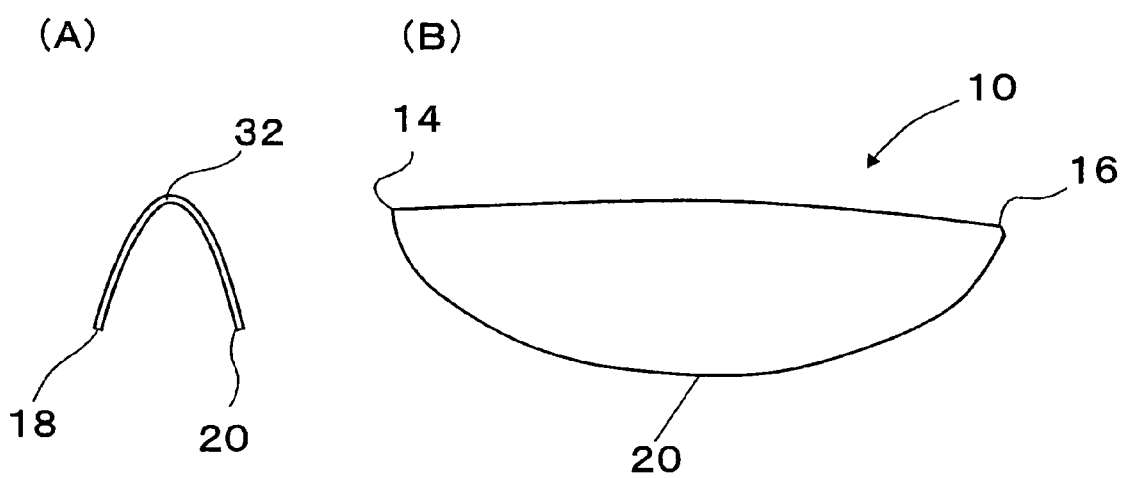
FIGS. 3(A) and 3(B) show an interlabial pad according to the embodiment.

FIG. 2 shows a schematic cross-sectional view taken along line X1-X2 of FIG. 1. The interlabial pad 10 comprises a liquid permeable surface side sheet 26 contacting the wearer's body side surface 22, that is, the inner walls of labia; a permeable or non permeable back side sheet 30 facing the opposite body side face 24, that is, the wearer's clothing side; and an absorbent body 28. The interlabial pad 10 is a laminated type pad, whose surface side sheet and back side sheet are joined together outside the edge of the absorbent.

The surface side sheet 26 and the back side sheet 30 may be joined by heat sealing only or in combination with a hot melt adhesive. The interlabial pad 10 is not limited to the above-mentioned laminated type structure, but may be an enclosed type structure, in which a water impermeable material is positioned under an absorbent and a water permeable sheet covers them entirely.

The interlabial pad 10 shown in FIG. 1 and FIG. 2 can be folded in two along the line from front 14 to rear 16 on Y-axis so that the central part 32 will be on the exterior. Then, the surface side 26 on the body side surface 22 is facing the upper side (or outside). On the other hand, the opposite body side surface 24 is facing the lower side and the back side sheet 30 is facing inside of the folded pad. In such structure, the surface side sheet 26 contacts the surface of the labia and the right and left sides of the pad contact the right and left sides of the labia respectively. Therefore, when the right and left sides of the labia are moved with the wearer's body motions, the interlabial pad changes in form by being forced from right and left. Consequently, the flexibility of the interlabial pad 10 plays an important role in reducing wearer discomfort.

Figure 4:
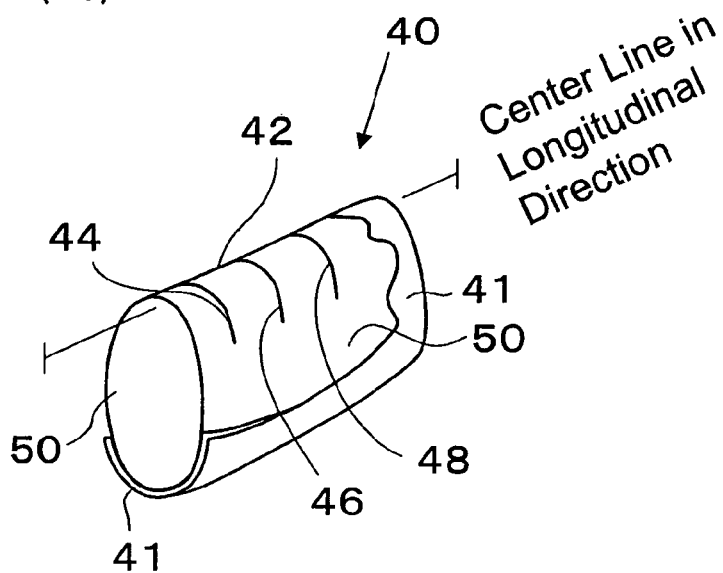
FIGS. 4(A) and 4(B) show an interlabial pad of an embodiment of the present invention.
Figure 4:
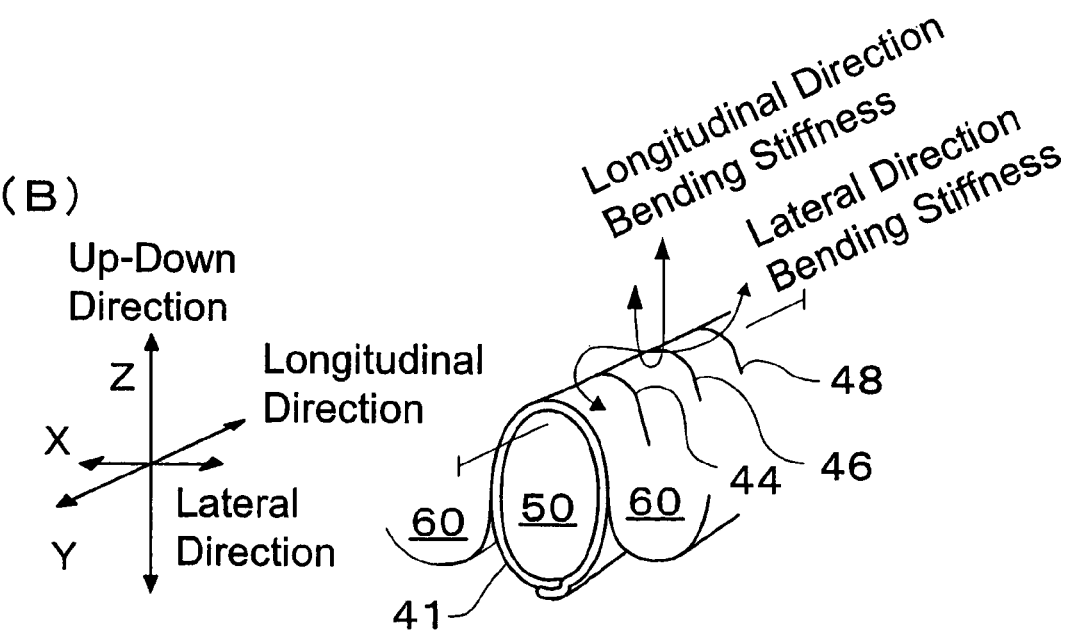

(A) in FIG. 4 shows an example of cylindrical interlabial pad 40 extending lengthwise with an oval cross-section. The bending elements which extend in the vertical direction in the interlabial pad 40 refer to bending elements 44, 46 and 48 shown by the lines extending in the vertical direction in the center 42 of the interlabial pad 40 in the figure. These bending elements are made in an absorbent body 50 and the absorbent body 50 is covered in covering material 41. When the interlabial pad 40 is arched with the central part on the exterior, these bending elements 44, 46 and 48 will open. That is, each fold resistance of 44, 46 and 48, located just below the wearer, is considered to be low as the volume of the absorbent body in the portion is smaller than the other portions. Also, the compressive stress and tensile stress directed through the depth of the absorbent body by bending will be smaller due to the reduced thickness.

(B) in FIG. 4 shows the interlabial pad being worn. The interlabial pad 40, which consists of the absorbent body 50 covered in the covering material 41, is placed between the right and left labia 60. The direction of the bending shown by the U-shape arrow (lengthwise flexural rigidity P) in the drawing is opposite to the direction of the above-described bending to the central part on the exterior. As the bending elements 44, 46 and 48 are also easy to bend in the direction shown by the U-shape arrow, the bending deformation is concentrated on the bending elements. As a result, the same displacement quantity of the bending deformation of the whole of the interlabial pad as that of the bending deformation without the bending elements 44, 46 and 48 is gained by smaller force. Likewise, with regard to the direction of the bending shown by the S-shape arrow (breadthwise flexural rigidity Q) in (B) in FIG. 4, the same displacement quantity of the bending deformation can be gained by smaller force. Thus, the bending elements enable the absorbent body to change in form easily and concurrently reduce the flexural rigidity on the vertical surface, which is perpendicular to the parallel direction in the interlabial pad worn between the labia and the flexural rigidity on the surface determined by the parallel direction and the vertical direction. In addition, the bending elements have the effect on reducing the flexural rigidity of the interlabial pad in directions and on surfaces other than the above.

Figure 5:
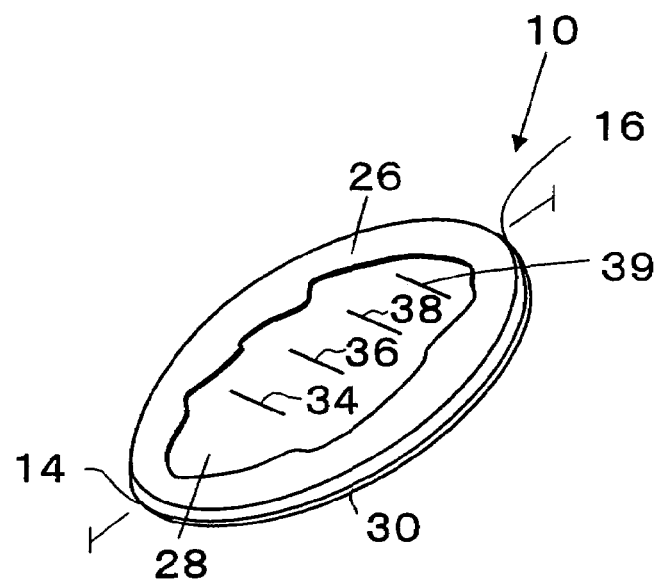
FIGS. 5(A) and 5(B) show an interlabial pad of an embodiment of the present invention.

(A) in FIG. 5 shows the interlabial pad 10 of another embodiment of the present invention. A part of the surface side sheet 26 is cut away to show the covered absorbent body 28 and bending elements 34, 36 and 38 created in the absorbent body. In this embodiment, the covering material is formed by joining the surface side sheet 26 and the back side sheet 30 together at each edge. The absorbent body 28 of such sheet-type interlabial pad 10 also has the same shape as the sheet. In the absorbent body 28, the bending elements 34, 36 and 38 are arranged parallel with each other, starting near the front 14 toward the rear 16 so that the bending elements cross the center line (or the central part) of the interlabial pad. This interlabial pad 10 is worn between the labia as shown in (B) in FIG. 5.

(B) in FIG. 5 shows the interlabial pad 10 which is folded in two so that both sides of the back side sheet 30 come into contact with each other and the surface side sheet 26 which contacts the right and left labia 60. This state is similar to the state of the cylindrical interlabial pad worn between the labia, shown in (B) in FIG. 4. In (B) in FIG. 5, the U-shape arrow and the S-shape arrow show the direction of each bending. Similar to the above, the bending elements reduce the fold resistance, which makes the pad easy to bend in each direction.

As shown in (B) in FIG. 5, the interiabial pad is worn being folded along the center line lying in the parallel direction so that the surfaces of the covering material facing the clothing (back side sheet 30) face each other. The parallel direction and the vertical direction are determined in relation to the placing or wearing the interlabial pad, however, for such an interlabial pad, the directions may determined with the pad being laid out flat as shown in (A) in FIG. 5. In such cases, a lengthwise direction (on the line from the front 14 to the rear 16), which is nearly parallel in the parallel direction can be used as the parallel direction and a breadthwise direction defined as the direction from the right 18 to the left 20 of the interlabial pad can be used as the vertical direction. The shape of the folded interlabial pad makes it easy for the body side surface of the right and left interlabial pad, which contact the right and left sides of the labia respectively and are symmetrical with respect to a lengthwise center line, to follow the changes in form of the right and left labia with the wearer's body motions, which will reduce the occurrence of gaps between the vestibule floor or the inner walls of the labia and the interlabial pad. The bending elements 34, 36, 38 and 39 of this shape, which extend breadthwise, seem to extend vertically in the drawing of the interlabial pad worn between the labia, however, they extend breadthwise when the interlabial pad is laid out flat as shown in (A) in FIG. 5.

The flexural rigidity of the interlabial pad which has the bending elements extending breadthwise so as to cross at least a lengthwise center line of the absorbent body can be 1.5 mN or less and more preferably, 1.0 mN or less for a lengthwise direction. The value of the flexural rigidity is measured with Gurley measuring apparatus. The samples for measuring were taken from the central part of the interlabial pad. The samples for measuring a lengthwise flexural rigidity were 38 mm lengthwise by 25 mm breadthwise and for the breadthwise flexural rigidity, 38 mm breadthwise by 25 mm lengthwise.

"Extend breadthwise above" may mean to lie or move toward the right and/or left side of the interlabial pad and is not required to be parallel or nearly parallel in a breadthwise direction. Likewise, "extend lengthwise above" may mean to lie or move toward the front 14 and/or the rear 16 of the interlabial pad and it is not required to be parallel or nearly parallel in a lengthwise direction. The bending elements can be provided on the covering material of the absorbent body as well as on the absorbent body.

Generally, it is preferable that a bending element has a length of 3 to 30 mm and a breadth (thickness) of 5 mm or less. The preferable distance between parallel adjacent bending elements (pitch) is 3 to 20 mm.

Figure 6:
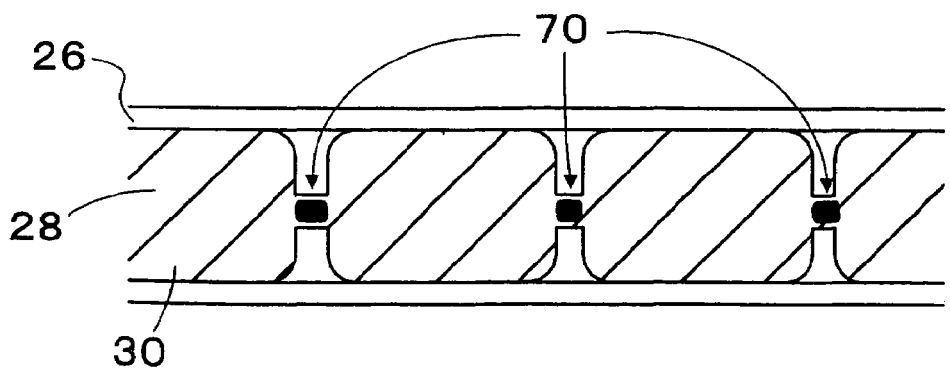
FIG. 6 illustrates a bending element created by embossing, which can be used in an embodiment of the present invention

FIG. 6 shows an example of the bending elements. The absorbent body 28 covered with the surface side sheet 26 and the back side sheet 30 is compressed at the bending elements 70. Such compressions can be made by embossing. For example, thrust processing or embossing in which the pads are drawn between rollers having protrusion patterns and flat patterns in order to provide the pad with a density difference. Other methods in which compressed parts are made by pressing using protrusion and flat parts making a difference in stiffness between the compressed parts and the other parts is made can also be used.

Figure 7:
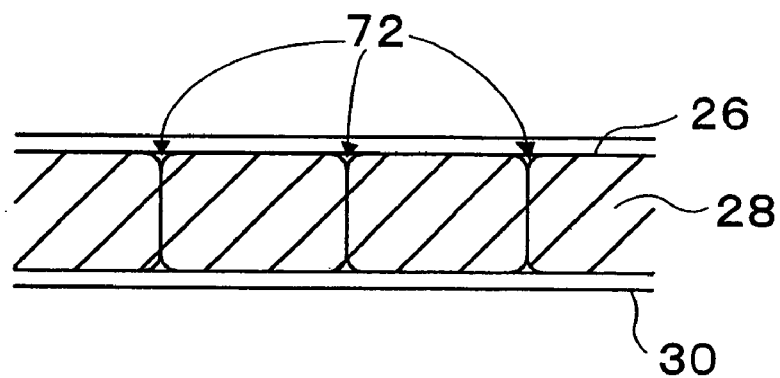
FIG. 7 illustrates a bending element created by slit processing, which can be 5 shows used in an embodiment of the present invention.

FIG. 7 shows a bending element made by slitting. The absorbent body 28 covered with the surface side sheet 26 and the back side sheet 30 is cut at the bending element 72. To cut through the absorbent body like this is more preferable as the fold resistance of the bending element is significantly low. Slitting without cutting through the absorbent body, which allows the fold resistance to be adjusted is also possible. Methods other than the above can also be used to make the bending elements. Parts having relatively low fold resistance can be the bending elements.

Figure 8:
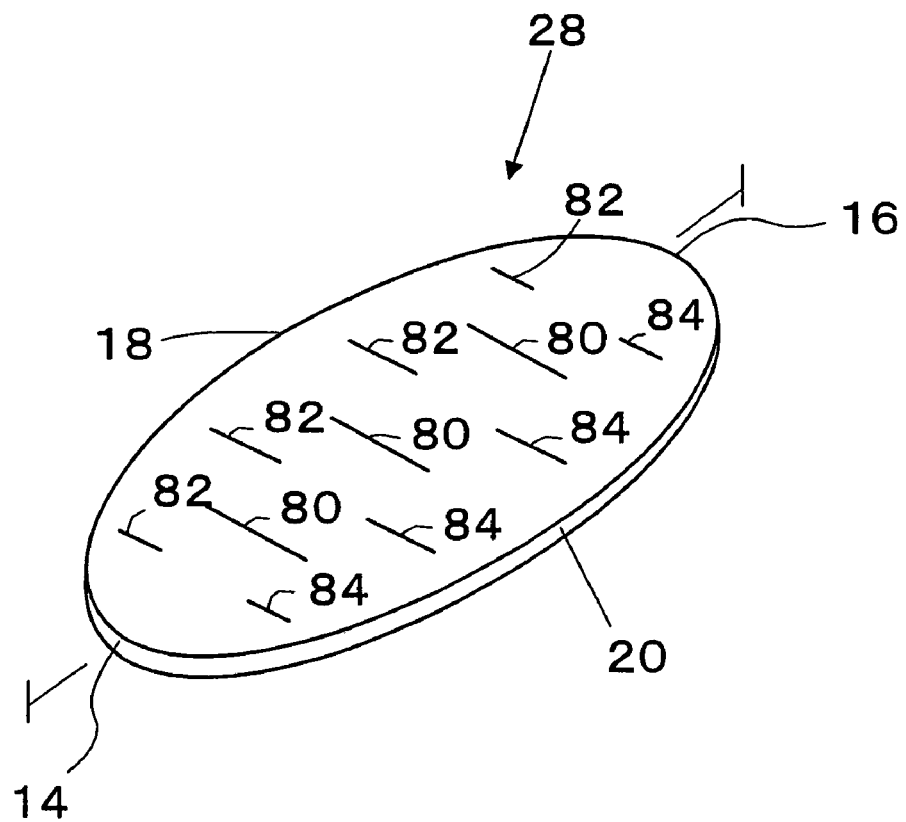
FIG. 8 shows the distribution (staggered arrangement) of bending element pieces which form a bending element included in the absorbent body of an interlabial pad of an embodiment of the present invention.

FIG. 8 shows an embodiment in which the bending element pieces, that is, bending elements are arranged in a staggered arrangement in the absorbent body 28. To cover the absorbent body 28 with the covering material (including the surface side sheet and the back side sheet) makes the interlabial pad 10. Bending element pieces 80 extending breadthwise are arranged in the central part, which is the center line neighborhood of the absorbent body along the parallel direction from the front 14 to the rear 16 corresponding to the front to the rear of the interlabial pad 10. Bending element pieces 82 extending breadthwise are arranged nearly parallel in the part between a right edge 18 of the absorbent body corresponding to the right of the interlabial pad and the center line. Bending element pieces 84, which are symmetrical to the bending element pieces 82 with respect to the center line, extending breadthwise are arranged nearly parallel in the part between a left edge 20 of the absorbent body corresponding to the left of the interlabial pad and the center line. The bending element pieces 82 and 84 arranged in the part between the edges of the absorbent body and the center line are not aligned with the bending element pieces 80 in the central part in a breadthwise direction but are staggered. Compared with arrangements in which the bending elements are placed parallel lengthwise, such arrangement has narrower intervals of the bending element pieces, consequently, it is considered that the flexural rigidity of the whole interlabial pad will be reduced evenly. Also, the flexural rigidity of the whole interlabial pad can be adjusted properly by changing the length of the bending element pieces.

Figure 9:
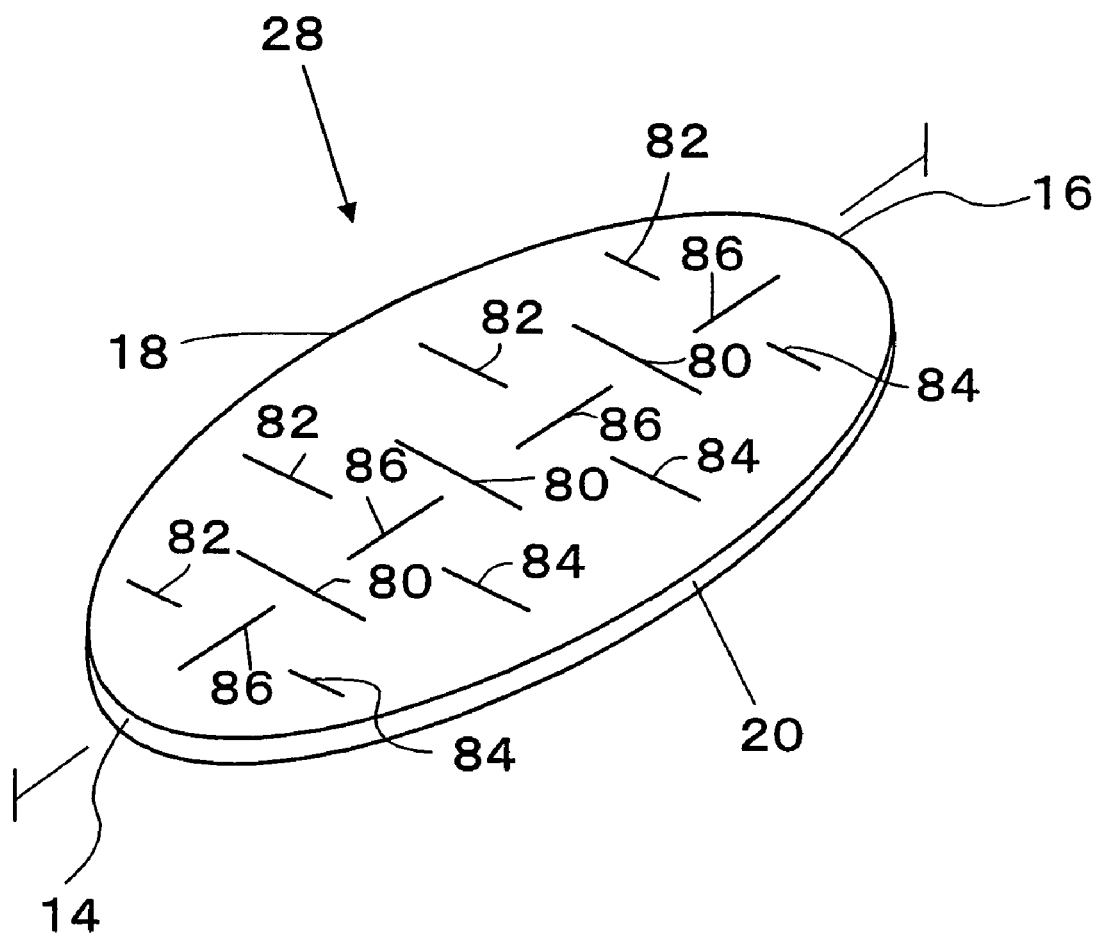
FIG. 9 shows the distribution (including bending element in the central part) of bending element pieces which form a bending element included in the absorbent body of an interlabial pad of an embodiment of the present invention.

FIG. 9 shows another embodiment of the present invention. In this embodiment, only the absorbent body 28 is shown in order to make it easier to understand the arrangement and distribution of the bending elements (including bending element pieces). Four bending element pieces 86, which are substantially parallel in a lengthwise direction, are arranged in the center line neighborhood extending from the front 14 to the rear 16. Three bending element pieces 80 are arranged, crossing the center line. These bending element pieces 86 and 80 do not cross each other. As is the case with FIG. 8, the bending element pieces 82 and 84, which are substantially parallel in a breadthwise direction, are arranged on the parts between the central part and the edges of the absorbent body. That is, FIG. 9 is different from FIG. 8 mainly because of the presence of the bending element pieces 86, which are substantially parallel in a lengthwise direction. Both FIG. 8 and FIG. 9 have symmetrical arrangements with respect to the center line. Therefore, few differences in the rigidity in the right and left sides are present, which will reduce the foreign feeling.

In addition, the bending element pieces 86, which are arranged lengthwise along the center line, make it easy to place the interlabial pad so that the central part will face the vestibule floor. This is considered to reduce the occurrence of leak of blood because the interlabial pad folded symmetrically keeps in close contact with the inner walls of the labia. Also, when the vestibule floor changes in form by being forced down with such motions as the wearer sitting down on a chair, not only the breadthwise bending elements, such as the bending element pieces 80, reduce a lengthwise flexural rigidity but also the downward compressive force can be easily converted into breadthwise compressive force starting from a lengthwise bending elements, reducing the foreign feeling to the wearer even more. If a lengthwise bending elements (the bending element pieces 86) are made by slitting, the pad can change in form more easily when being compressed downward by a greater force as the absorbent body material on both sides of the bending element can change in form to separate from each other.

The preferable downward compressive rigidity of the interlabial pad worn between the labia is 50 cN/cm$^2$ or less, and more preferably, 30 cN/cm$^2$ or less. The compressive rigidity was measured in the vicinity of the center of the interlabial pad, compressing a constant-rate extension digital force gauge by 3 mm downward at the rate of 100 mm/min.

Figure 10:
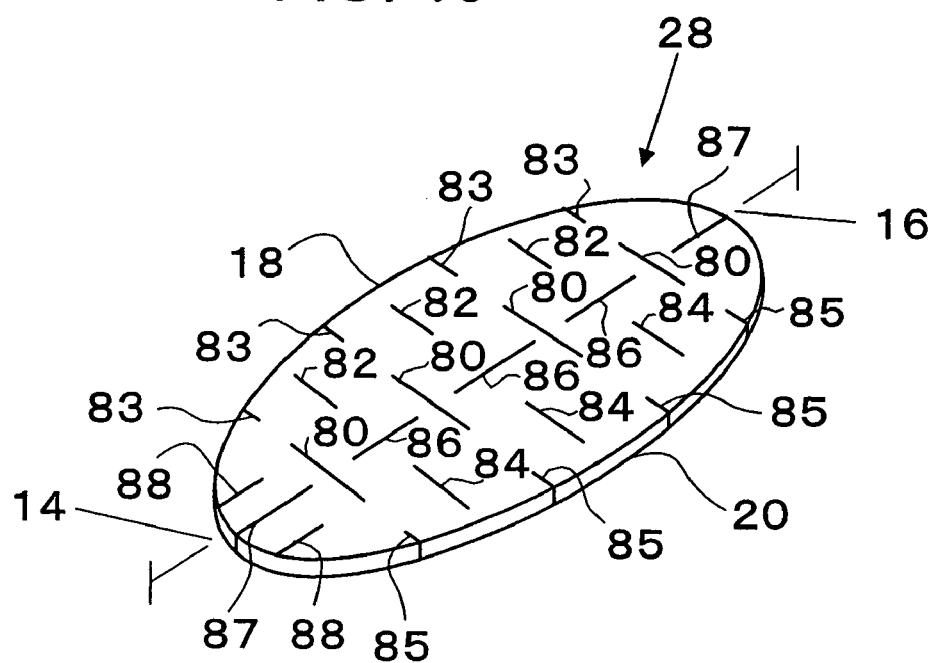
FIG. 10 shows the distribution (bending element passing through the edges) of bending element pieces which form a bending element included in the absorbent body of an interlabial pad of an embodiment of the present invention.

FIG. 10 shows another embodiment of the present invention. In this figure, also, only the absorbent body 28 is shown in order to make it easier to understand the shape and arrangement of the bending elements (including bending element pieces). In the center line neighborhood extending from the front 14 to the rear 16, three bending element pieces 86, which are substantially parallel in a lengthwise direction and do not reach the edges of the absorbent body 28, are arranged and two bending element pieces 87, which reach the edges of the absorbent body 28, are arranged at the front and rear respectively. In addition, two bending element pieces 88, which reach the edges of the absorbent body 28, are arranged substantially parallel with the front bending element piece 87, at both sides of the bending element piece 87 and slightly apart from the bending element piece 87. Four bending element pieces 80, which are substantially parallel in a breadthwise direction, are arranged, crossing the center line. These bending element pieces 86 and 80 do not cross each other. As is the case with FIG. 8 and FIG. 9, the bending element pieces 82 and 84, which are substantially parallel in a breadthwise direction, are arranged on the parts between the central part and the edges of the absorbent body. Also, four bending element pieces 83 and 85 each, which are substantially parallel in a breadthwise direction and reach the edges of the absorbent body 28, are arranged near the right and left edges.

Since an interlabial pad is worn in an area which is hard to see, the wearer has to feel for the proper placement to wear the pad. The edges of the interlabial pad may come into contact with the inner walls of the labia or the pudenda. Therefore, it is preferable to reduce the rigidity of the pad so as not to cause the wearer to have discomfort or a foreign feeling. Arranging the bending elements (including bending element pieces) so as to reach the edges of the absorbent body reduces the rigidity of the edges sufficiently. If the bending elements are made by slitting, the bending elements in the absorbent body can separate to open outward from bending elements, which will reduce the wearer's discomfort and foreign feeling.

The front end of the interlabial pad tends to contact the clitoris while the rear of the interlabial pad tends to contact the ostium vaginae or the anus. It is preferable that the bending elements (including bending element pieces) at the front and rear of the interlabial pad, which tends to contact these sensitive parts, at least reach the edges of the absorbent body.

Figure 11:
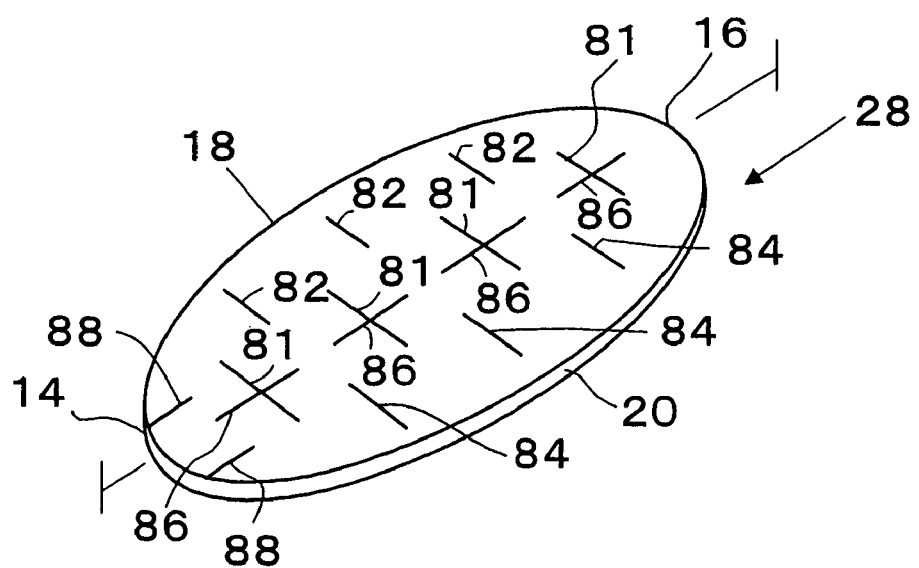
FIG. 11 shows the distribution (bending element crossing in the center) of bending element pieces which form a bending element included in the absorbent body of an interlabial pad of an embodiment of the present invention.

FIG. 11 shows another embodiment of the present invention. In this figure, also, only the absorbent body 28 is shown in order to make it easier to understand the shape and arrangement of the bending elements (including bending element pieces). In the center line neighborhood extending from the front 14 to the rear 16, four bending element pieces 86, which are substantially parallel in a lengthwise direction and do not reach the edges of the absorbent body 28, are arranged. In addition, the bending element pieces 88, which reach the edges of the absorbent body 28, are arranged substantially parallel in a lengthwise direction, at a specified distance from the center line. Four bending element pieces 81, which are substantially parallel in a breadthwise direction, are arranged, crossing the center line. These bending element pieces 86 and 81 cross each other.

With such a structure, even when the vestibule floor changes in form by being forced down with such motions as the wearer sitting down on a chair, the downward compressive force can be easily converted into multidirectional compressive force starting from the intersecting points of a lengthwise and breadthwise bending elements, which will reduce the foreign feeling to the wearer. If slit-processing the bending elements, the shape deformation is caused so as to separate from the bending element to the downward direction of the absorbent body, and so the deformation is easily caused more to the lower compression force. The bending elements forming the intersecting points are not limited to two but can be more than two.

Figure 12:
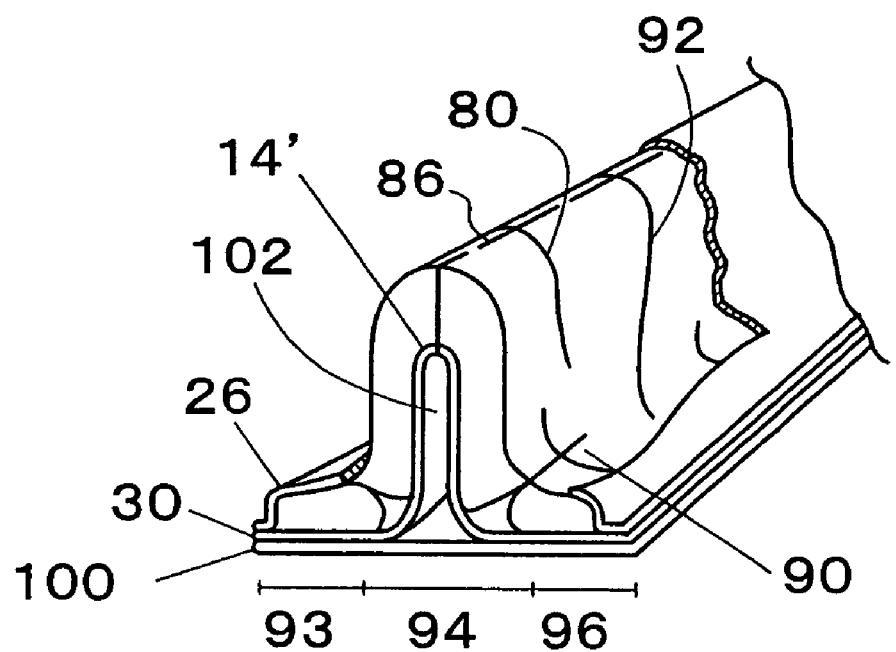
FIG. 12 is a perspective view of an interlabial pad of an embodiment of the present invention, to which a mini sheet piece is attached to the opposite side surface to body.

FIG. 12 shows another embodiment of the present invention. This is a three-dimensional perspective view of the interlabial pad which has a mini sheet piece 100 on its back side sheet 30 facing the opposite side surface to body. A part of the back side sheet 26 is shown cut away in order to make it easier to understand the shape and arrangement of the bending elements (including bending element pieces) in the absorbent body 28 covered with the covering material. In the center line neighborhood, a bending element piece 86 is positioned, substantially parallel in a lengthwise direction, not reaching the edges of the absorbent body 28. In addition, a bending element piece 90 (a bending element extends lengthwise in the junction) is positioned substantially parallel in a lengthwise direction, at a specified distance from the center line, near the front 14. A bending element piece 80, which is substantially parallel in a breadthwise direction, and a bending element piece 92, which is longer than the bending element piece 80, extends at a specified angle with respect to the breadthwise direction and changes its orientation into a breadthwise direction near the finger insert hole, are positioned to cross the center line. These bending element pieces 80 and 92 cross the bending element pieces 86 in the central part respectively. The absorbent body 28 can be divided and named breadthwise to an extension part 93, a long protrusion part 94 and an extension part 96 starting the left side in the figure (from the right side of the wearer).

When the mini sheet piece 100 is attached in this manner, the interlabial pad can be worn easily by inserting the finger into a slot 102. More specifically, when putting in place, with the finger contacting the side of the interlabial pad facing the clothing, in the vicinity of a lengthwise center line, pushing the labia open, the interlabial pad can be placed securely in the vestibule floor. Therefore, it is possible to prevent leak of blood by avoiding creating a gap between the vestibule floor or the inner walls of the labia and the side of the interlabial pad facing the body. It is also preferable that a finger insert hole to secure the finger in a lengthwise direction of the back side sheet is formed by providing a the mini sheet piece which is attached with more than one bonded part on both sides along the lengthwise direction and more than one part which is not bonded along the breadthwise direction so as to fit the finger in the vicinity of a lengthwise center line.

An interlabial pad which is provided with a mini sheet piece having a finger insert hole on the side facing the body makes it possible to place the interlabial pad in a secure position because by inserting the finger with the palm side of the fingertip contacting the back side sheet, the sensitive fingertip can sense the position of the ostium vaginae, which is concaved. This will prevent leak of blood.

To place the interlabial pad, the wearer inserts her finger into the finger insert hole so that the interlabial pad is supported by the finger wrapped in the slot 102. When the interlabial pad is guided to the interlabial space from the front side (ventral side), the palm may contact the front side (opposite side to the direction of finger insertion) of the interlabial pad. Even in such case, because the bending element (bending element piece) 92, which extends breadthwise is made at least in the absorbent body, the front side of the interlabial pad can change in form easily so as not to change the relative position of the finger and the interlabial pad. After wearing the interlabial pad between the labia, in pulling the finger out from the slot 102, some wearers pull out their finger with their finger bent, which causes the palm to contact the front side (opposite side to the direction of finger insertion) of the interlabial pad. Even in such case, because the bending element (bending element piece) 92, which extends breadthwise is made at least in the absorbent body, the front side of the interlabial pad can change in form easily so as not to change the relative position of the finger and the interlabial pad in pulling out the finger.

As shown in FIG. 12, the long protrusion part 94, which is placed between the labia, maintains the closeness to the inner walls of the labia and the extension part 96, which extends breadthwise from both sides of the long protrusion part 94, cover the pudenda in intimate contact. This will increase the contact area, which prevents leak of blood. At the junction (or border) of the long protrusion part 94 and the extension part 96, bending element pieces, which extends lengthwise are made at least in the absorbent body. This makes it easy to maintain the extension part 96 perpendicular to a vertical direction in use so that the absorbent body surface can absorb the menstrual flow excreted downward in a large quantity.

Figure 13:
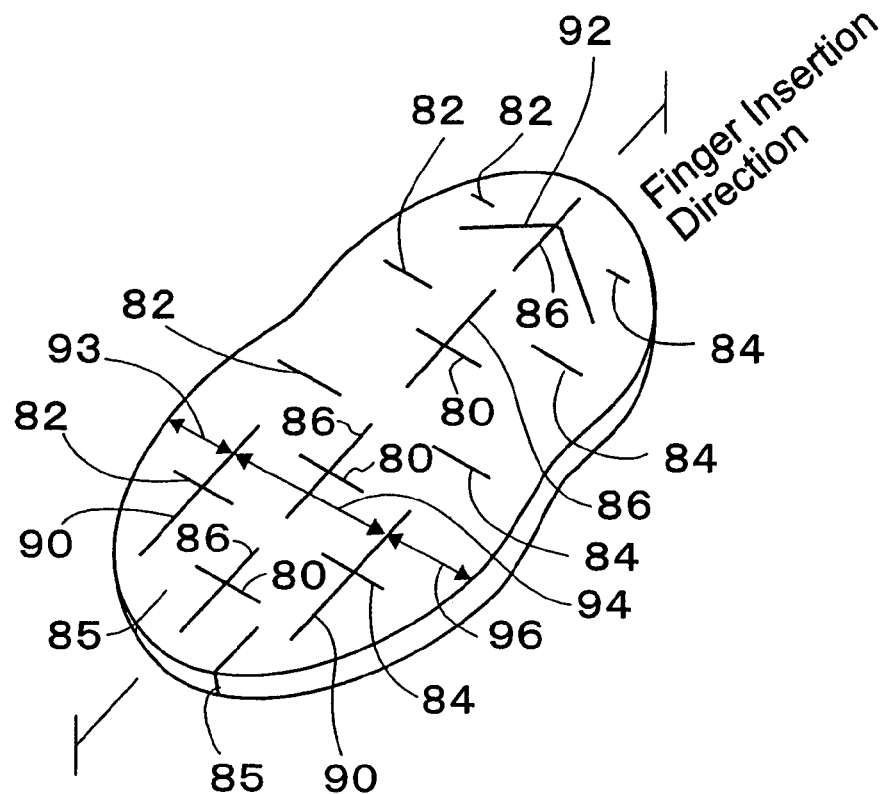
FIG. 13 is a perspective view of the absorbent body (laid out flat) of the interlabial pad of the embodiment shown in FIG. 12.

FIG. 13 is a perspective view of the interlabial pad of the embodiment shown in FIG. 12. The absorbent body 28 is taken out from the covering material and laid out flat. The extension part 93, long protrusion part 94 and extension part 96 are shown by double-headed arrows respectively. The bending element piece 90 extending lengthwise in the above-described junction is just on the border between the extension part 93 and the long protrusion part 94. In addition, In this figure, the bending element piece 92 extending breadthwise near the above-described finger insert hole is shown in a "V" shape oriented to the direction of finger insertion X. Though the two segments of the bending element piece 92 are joined in the central part, bending element piece can be separated into two in the central part. In this case, this bending element piece has a specified angle including a right angle with respect to the lengthwise or breadthwise direction.

Figure 14:
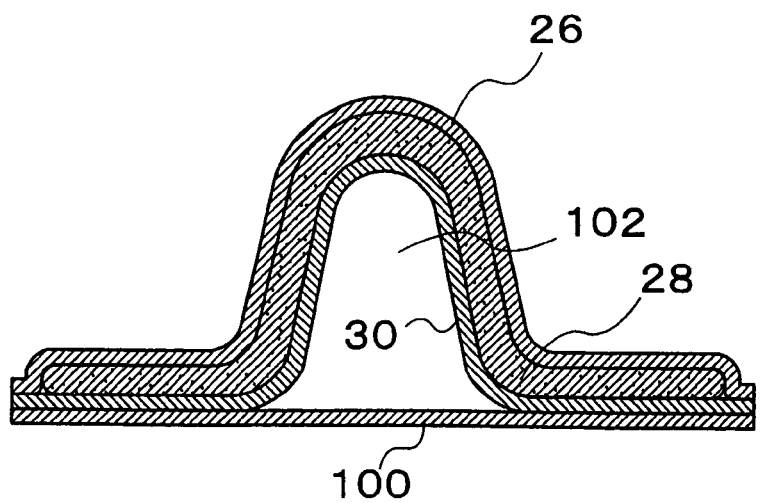
FIG. 14 is a cross-sectional view of the interlabial pad of an embodiment of the present invention, to which a mini sheet piece is attached to the opposite side surface to body.
Figure 15:
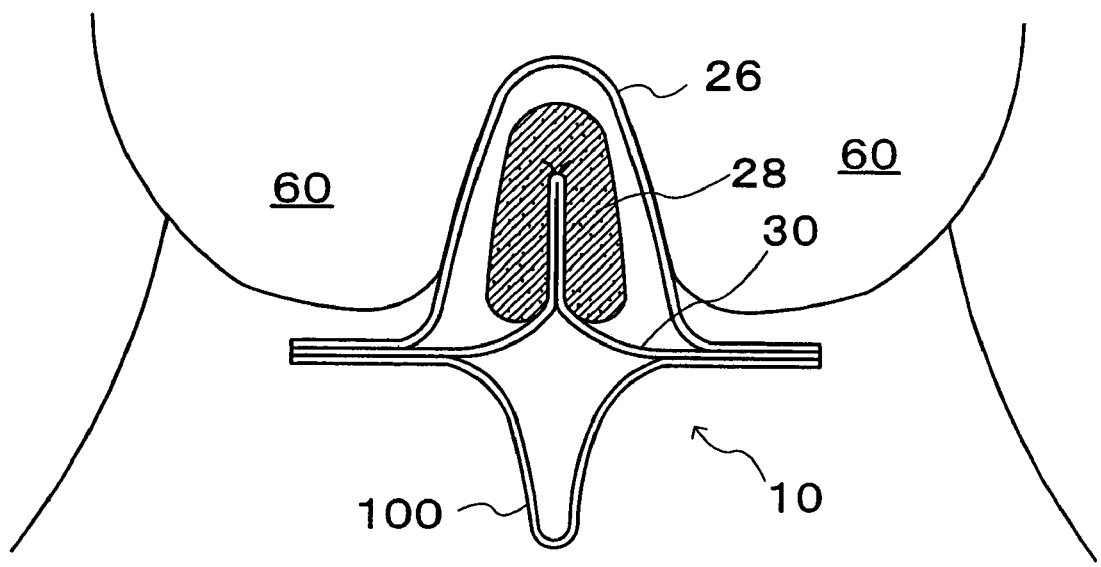
FIG. 15 is a cross-sectional view of the interlabial pad of an embodiment of the present invention, to which a mini sheet piece is attached to the opposite side surface to body, being worn.

FIG. 14 is a cross-sectional view of the interlabial pad having the mini sheet piece 100 of the present invention. The absorbent body 28 is covered with the surface side sheet 26 and the back side sheet 30. FIG. 15 shows the interlabial pad with the mini sheet piece 100 in FIG. 14 worn between the labia 60. The surface side sheet 26 is placed between the labia and the absorbent body 28 is covered with the surface side sheet 26 and the back side sheet 30. The mini sheet piece 100 is pushed out from the slot 102 and hangs slack downward. The details of the materials for these components will be described later.

Figure 16:
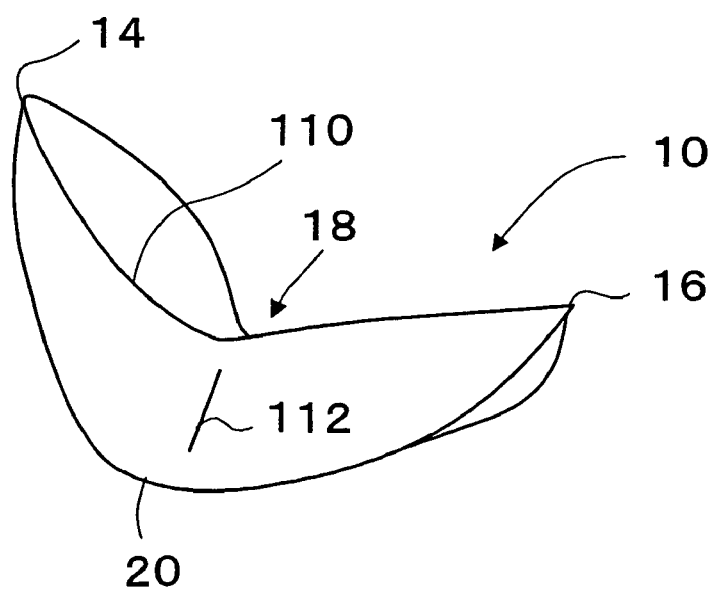
FIG. 16 is a perspective view of the interlabial pad of an embodiment of the present invention bent to the right.
Figure 17:
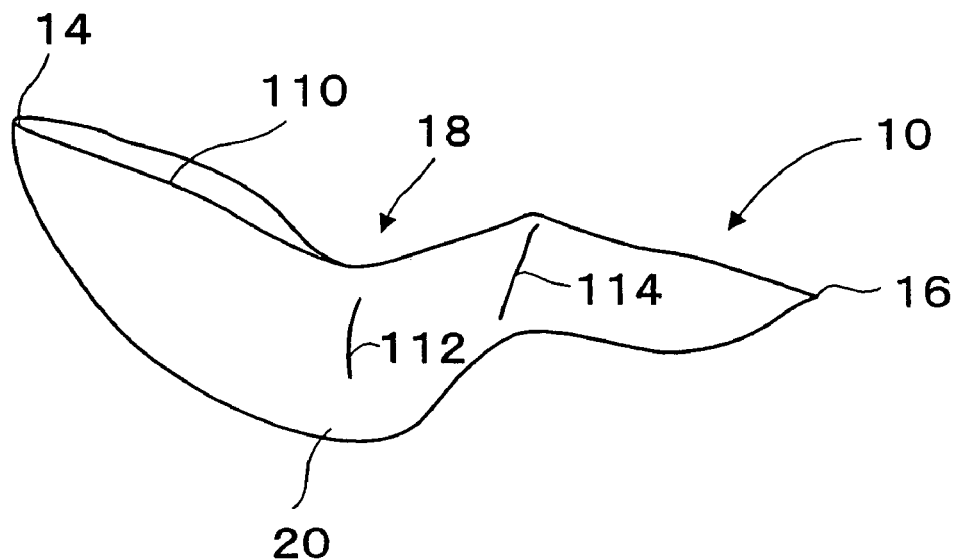
FIG. 17 is a perspective view of the interlabial pad of an embodiment of the present invention bent to the right and left.
Figure 18:
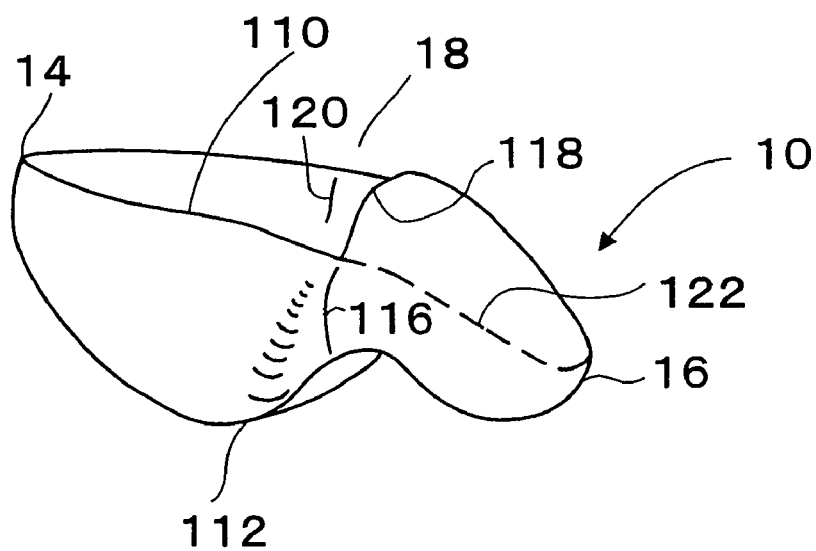
FIG. 18 is a perspective view of the interlabial pad of an embodiment of the present invention bent with the rear part downward.

FIGS. 16 to 18 show in diagrammatic form how the interlabial pad changes in form when the specified bending element pieces are arranged in place. FIG. 16 shows a schematic diagram of the interlabial pad bent to the right. The interlabial pad 10 has a bending element piece 110 in the center line neighborhood extending from the front 14 to the rear 16 (or in the long protrusion part). Therefore, it is considered that the interlabial pad 10 can be easily folded in two to contact the vestibule floor, which will enhance the closeness. In addition, between the left edge 20 of the interlabial pad 10 and the central part, a bending element piece 112 extends breadthwise. Likewise, a similar bending element piece extends on the right side 18 of the interlabial pad 10. These bending element pieces allow the pad to bend easily.

FIG. 17 shows the interlabial pad bent to the right and left in an "S" curve. The pad is bent with a bending element piece 112 on the exterior, orienting the front 14 to far side and is also bent with the bending element piece 114 on the interior, orienting the front 16 to this side. This interlabial pad 10 also has a bending element piece 110 in the center line neighborhood. It is considered that the appropriate arrangement of the bending element pieces makes such complicated bending easy.

FIG. 18 shows the interlabial pad 10, slightly unfolded and bent so that the part near the rear 16 is oriented downward. In this case, the bending element piece 110 makes it easy to fold the pad in a center and the bending element pieces 116 and 118 make it easy to fold the pad downward. These bending element pieces extend slightly curving at a specified angle with respect to the lengthwise direction.

The detailed description of materials for each component of the interlabial pad of the present invention will be given below.

As shown in FIG. 14, the interlabial pad 10 consists of the surface side sheet 26, the absorbent body 28, the back side sheet 30 and the mini sheet piece 100. The surface side sheet 26 is made of a permeable sheet, the absorbent body 28 is made of a material which can absorb body fluids and the back side sheet 30 is made of a water impermeable sheet. The mini sheet piece 100 can be made of the same materials as for the permeable sheets or water impermeable sheets. For the interlabial pad, an adhesive can be applied to a part of the mini sheet piece to enhance the closeness to the body in use. The detailed description of these components and the materials are as follows:

[Components of the Interlabial Pad]

<Permeable Sheet>

The surface side sheet 26 of the interlabial pad facing the body is water permeable. For the water permeable sheet, materials which are hydrophilic and non-irritant to the skin are used. Examples of these materials include materials which are made of any single or combination of nonwoven fabrics made by melt blowing, spun bonding, point bonding, through air, needle punching, wet-type spun lace, foam film, and so on.

Examples of fibrous sheets include sheeted fabrics which are any single or mixture of fibers made of any single of rayon, acetate, cotton, pulp or synthetic resin, or fibers made by combining these fibers to form sheath-core structure.

Among the materials, considering the liquid mobility from the inner face of the labia, chemical stimulation by a surface active agent, and adhesion with the inner wall of the labia, it is preferable to laminate rayon with 1.1 to 4.4 dtex fineness and 7 to 51 mm fiber length by 40 to 80% of a total specific weight per unit area on the body face side, and to laminate a mixture of rayon with 1.1 to 4.4 dtex fineness and 7 to 51 mm fiber length by 14 to 42% of a total specific weight per unit area and PET with 1.1 to 4.4 dtex fineness and 7 to 51 mm fiber length by 6 to 18% of a total specific weight per unit area on the garment face side. After laminating them so that the total specific weight per unit area of the two layers becomes 20 to 60 g/m$^2$, the fibers are entangled by water-flow interlacing treatment and then dried to prepare spun lace nonwoven fabric with the thickness of 13 to 0.50 mm. The spun lace nonwoven prepared as described is preferable. At this time., by mixing PET on the garment face side, bulkiness can be easily maintained even if the permeable sheet becomes wet. Therefore, adhesion between the inner wall of the labia can be maintained.

<Absorbent>

As the absorbent contained in the interlabial pad, any single or combination of materials, such as pulp, chemical pulp, rayon, acetate, natural cotton, super absorbent polymer, fibrous super absorbent polymer and synthetic fiber, can be used. Mixtures of required composition are formed into sheets by known techniques, such as crimping by embossing and entangling by needling, and as required, can be appropriately adjusted by controlling the bulk, layering, folding or the like.

Sheet materials may be used after processed into sheets or powder, not being limited by its application.

It is preferable for the absorbent body, although any material can be used as long as it is capable of absorbing and holding liquid (body fluid), to be bulky, hard-to-be deformed, less chemically stimulant, and highly flexible to fit into the labia. Specifically, a nonwoven sheet in which, 50 to 150 g/m$^2$ of pulp selected from the range of the fiber length of 1 to 10 mm is laminated on the garment face side and, on the body face side, 150 to 250 g/m² of a mixture obtained by mixing 60 to 90% of rayon with 1.1 to 4.4 dtex fineness and 20 to 51 mm fiber length with 40 to 10% of natural cotton by this mixing ratio is laminated, which then to be formed into a sheet by dotted embossing to have 2 to 10 mm bulkiness, and more preferable to have 3 to 5 mm bulkiness. Thereby, liquid can be easily transmitted from the body face side to the garment face side resulting in the improvement of the absorbing and holding capacity. Furthermore, by providing a mesh spun lace nonwoven fabric of rayon with 1.1 to 4.4 dtex fineness and 25 to 51 mm fiber length by a specific weight per unit area of 15 to 40 g/m², the liquid transmitted from the body face side can be dispersed by the mesh spun lace to be induced to almost all over the region of the pulp layer. Therefore, more liquid can be effectively absorbed.

<Water Impermeable Sheet>

For the back side sheet 30 used for the interlabial pad, water impermeable sheets are used. As the materials for the water impermeable sheets, materials which can prevent the menstrual flow contained in the absorbent body from leaking out of the interlabial pad can be used. Using moisture-permeable materials will reduce the hot and muggy feeling, which will reduce the discomfort in use.

Examples of such materials include sheet films made of synthetic resins which are formed into membranes, breathing films made by drawing with inorganic fillers, paper, laminated materials made by combining nonwoven fabrics and films and porous waterproof sheets having 0.1 to 0.6 mm-diameter openings covering 10 to 30% of the total area with capillaries located to extend toward the absorbent.

Additionally, in considering flexibility so as not to degrade the feel in use, a film having a weight per unit area of 15 to 30 g/m² and mainly consisting of low density polyethylene (LDPE) resin which has a density of 0.900 to 0.925 g/cm³ can be used as a preferred example. More preferably, protrusions can be made on the above films by embossing in order to reduce the rate of contact and lower the frictional resistance. This will reduce the possibility that the interlabial pad may fall off from the labia due to the high friction between the surfaces of the water impermeable sheet, or between the water impermeable sheet and a pad used in combination with the interlabial pad or underwear.

<Mini Sheet Piece>

For a mini sheet piece, the same materials as for above-described water permeable sheets and water impermeable sheets can be used and it is preferable to use materials having at least breadthwise extensibility or flexibility.

By using such materials for the mini sheet piece, even if the wearer's finger is larger than the provided finger insert hole, the mini sheet piece can stretch at least breadthways corresponding to the wearer's finger size. This allows the wearer to use the interlabial pad effectively regardless of the wearer's finger size.

Examples of materials essentially having elasticity include styrene-butadiene-styrene block copolymer (SBS), styrene-isoprene-styrene block copolymer (SIS), synthetic rubber such as urethane rubber, films made from amorphous olefin resin having a density of 0.88 to 0.900 g/cm³, opening foam film and net. Woven fabrics or fabrics in which spun filaments made from synthetic rubber are interwoven can also be used. In addition, a spun bond nonwoven fabric, a melt blown nonwoven fabric and expanded foam sheet which mainly made from synthetic rubber can also be used.

In considering a soft feel in use, a preferred example is a porous foam film made from SEBS, adjusted to be 15 to 40μ thick and constructed to have pores of 0.28 to 1.77 mm² covering 40 to 70% of the total area.

Examples of nonwoven fabric include materials which mainly consist of heat shrinkable compound synthetic fibers having a high-melting core part and a low-melting sheath part, such as PE/PP, PE/PET, PP/PP; including a spun lace nonwoven fabric whose fibers are entangled by water streams, shrink-type nonwoven fabric whose fibers are shrunk by reheating air processing and so-called extensible spun bond, which is a sheet made from continuous long fiber by heat sealing and forced tentering in the longitudinal direction.

More specifically, a shrink-type nonwoven fabric which mainly consist of heat shrinkable compound synthetic fibers having a fineness of 1.1-4.4 dtex, a length of 7-51 mm, high-melting core part and low-melting sheath part, such as PE/PP, PE/PET, PP/PP and adjusted to have a weight per unit area of 10 to 60 g/m² is a suitable material having a suitable softness and drape. Laminated materials made of the materials described above can also be used.

When using non-extensible materials which are processed to have extensibility, the examples of the materials include any single or compound of nonwoven fabrics which mainly consist of heat shrinkable compound synthetic fibers having high-melting core part and low-melting sheath part, such as PE/PP, PE/PET, PP/PP, including a bulky through air nonwoven fabric which is processed by hot air, a spun lace nonwoven fabric whose fibers are entangled by water streams, spun bond nonwoven fabric sheets made by layering continuous fiber, a needle punch nonwoven fabric whose fibers are entangled with needles and a SMS nonwoven fabric formed into sheets by multi-layering spun bond and melt blown fabrics, and opening foam film and films mainly consisting of PE resin.

It is also possible to provide the above-described materials with extensibility using corrugate processing, in which the material is placed between male-female molds and embossed by heat, temperature and pressure. More specifically, the examples include a through air nonwoven fabric which mainly consists of compound synthetic fibers adjusted to have a fineness of 1.1 to 4.4 dtex and a weight per unit area of 10 to 60 g/m² and applied corrugate processing to have breadth-ways extensibility. Preferably, the male-female molds of the corrugate processing is arranged to achieve an extensibility at least 10%, and more preferably, to have an extensibility of 20 to 50%, yet more preferably, the processed material is extended by 30% with a load of 0.01 to 0.05 N/mm (Test condition: using tensilon tensile tester, velocity: 100 mm/min., chuck interval: 100 mm). For providing the materials with extensibility, methods such as making incisions or perforating can be used.

<Adhesive>

As the adhesives to connect (bond) each material, hot-melt adhesives which are generally used can be employed. Examples of such adhesives include pressure-sensitive hot-melt adhesives and heat-sensitive hot-melt adhesives. The pressure-sensitive hot-melt adhesives are made by melt blending tackifiers such as terpene resin and rosin resin and plasticizers such as wax with the main ingredient such as synthetic rubbers including SIS, SBS, styrene-ethylene butadiene-styrene block copolymer (SEBS) and styrene-ethylene propylene-styrene block copolymer (SEPS). Examples of heat-sensitive hot-melt adhesives include adhesives having base resin mainly consisting of olefin resin, such as poly-α-olefin. Among these various adhesives, considering the stability in application, it is preferable to use heat-sensitive hot-melt adhesives. Examples of heat-sensitive hot-melt adhesives having high stability in application include adhesives made by melt blending poly-α-olefin by 45 to 55 weight percent, plasticizer by 10 to 15 weight percent and tackifier by 35 to 45 weight percent. To the heat-sensitive hot-melt adhesives, antioxidant or antifluorescent can be added within a range of 0.1 to 1.0 weight percent.

[Structure of an Interlabial Pad Which is Also Biodegradable, Water Dispersible and Water Soluble]

It is possible and preferable that the interlabial pad of the present invention consists of biodegradable and/or water dispersible and/or water-soluble materials. Such interlabial pads can be dropped into toilets and flushed away, which allows the easy and clean disposal of used pads and reduces the refuse in toilet facilities.

In this Specification, "biodegradability" means that a substance is decomposed into gas such as carbon dioxide or methane, water, and biomass under anaerobic or aerobic condition according to the natural process under the existence of bacteria represented by actinomycetes and other microbes, and also means that the biodegradability (biodegradable rate and biodegradable degree) of the substance equals to a material naturally generated such as fallen leaves or a synthetic polymer generally recognized having the same biodegradability under the same environment. "Water dispersibility" means the same as water degradability, where there is no effect from the limited amount of water (menstrual blood) upon use, whereas in conditions of large amounts of water or under water flow, the fibers are easily dispersible into at least small pieces which cannot clog the toilet plumbing. "Water solubility" means the property of not being affected by limited amount of water (menstrual blood) upon use, but being soluble in large amounts of water or under a flow of water.

<Water Permeable Sheet>

As the materials for water permeable sheets, along with a spun lace nonwoven fabric, wet-process spun lacing nonwoven fabric selected from the nonwoven fabrics within a range of fiber length of 1 to 15 mm can be used. In addition to the above-described materials, resins which are biodegraded by hydrolysis process, such as polylactic acid, polybutylene succinate can also be used. For example, a melt blown nonwoven fabric which is made from polylactic acid and adjusted to have a weight per unit area of 20 to 60 g/m² or a spun bond nonwoven fabric adjusted to have a weight per unit area of 15 to 30 g/m² and a fineness of 1.1 to 3.3 dtex can be used. For each nonwoven fabric material, aperturing is optional.

As the other materials, the tow of synthetic fiber or of continuous fiber of the laminated body may be used by adjusting to a range of weight per unit area of 50 to 300 g/m² to ravel fiber each other.

<Absorbent Body>

As the materials for absorbent bodies, nonwoven fabric sheets made by needling can be used. Considering the biodegradability of super absorbent polymer, it is preferable to use carboxymethyl cellulose fibers.

<Water Impermeable Sheet>

As materials for water impermeable sheet, PVA films, film sheets made by applying water-repellent processing on one side, both sides or some parts of PVA films using silicone and so on, PVA films mixed with silicone, starch films, laminated paper consisting of films made of resins which are biodegraded by hydrolysis process, such as polylactic acid and polybutylene succinate, and tissue. The materials may be colored by mixing inorganic pigments within a range of 0.1 to 5% as required.

When maintaining leakage prevention in humid conditions and avoiding an excessive load on septic tank is taken into consideration, a preferred material is laminated paper made by laminating a film made from polylactic acid to tissue having a thickness of 10 to 20μ and a weight per unit area of 15 to 20 g/m², with a bonded area of 5 to 40% of laminated area.

<Mini Sheet Piece>

As materials for the mini sheet piece, films, a spun bond nonwoven fabric and a melt brown nonwoven fabric made from biodegradable resins, such as polylactic acid, polybutylene succinate; films and nonwoven fabrics made from water-soluble materials such as PVA and CMC; and water dispersible tissue and a spun lace nonwoven fabric mainly consisting of cellulose fibers, regenerated cellulose and others can be used.

It is preferable to use sheets of a spun bond nonwoven fabric or a melt blown nonwoven fabric, which mainly consist of biodegradable materials, are adjusted to have a fineness of 0.1 to 3.3 dtex and a weight per unit area of 15 to 40 g/m² and are subjected to the mechanical corrugate processing.

INDUSTRIAL APPLICABILITY

As described above, the interlabial pad of the present invention has a shape which allows the pad to be placed easily between the labia and consists of an absorbent body which absorbs body fluid and a covering material which covers the absorbent body. As the interlabial pad is characterized by having bending elements at least in the absorbent body, the interlabial pad can easily change in form starting from the bending elements (or be bent at bending elements), which can reduce both lengthwise rigidity and breadthwise rigidity of the interlabial pad worn between the labia. This will allow the interlabial pad to follow the change in form of the vestibule floor more effectively, reducing the foreign feeling caused by the wearer's body motions. In addition, as the closeness to the vestibule floor will be also enhanced, it is possible to prevent leak of blood.

What is claimed is:

1. An interlabial pad with a size, weight, and flexibility capable of being held between labia by a part or the whole portion of the interlabial pad naturally therebetween, having a first axis that is substantially parallel to an anteroposterior axis of a wearer, and a second axis which is included in a horizontal plane when the wearer is standing and perpendicular to the first axis, comprising:
   an absorbent body for absorbing body fluid, the absorbent body having a shape selected from the group consisting of elliptical-planar shapes, gourd-planar shapes and tear drop-planar shapes, the absorbent body having a plurality of bending elements each including a slit formed on a surface of the absorbent body, the bending elements each being provided in a prescribed position of the absorbent body with a lower bending strength compared to positions other than the prescribed position, wherein the absorbent body is formed into a sheet-like member having a thickness of 3 to 5 mm and comprising at least one of pulp, chemical pulp, rayon, acetate, natural cotton, super absorbent polymer, fibrous super absorbent polymer, and synthetic fiber;
   a plurality of first bending element pieces, each first bending element piece extending for a first prescribed length in a direction that is substantially parallel with the first axis, and the plurality of first bending element pieces including:
   i) first bending element pieces having the slit positioned along the center line of the absorbent body in parallel with the first axis,
   (ii) first bending element pieces having the slit arranged to reach a first peripheral edge of the absorbent body, and (iii) first bending element pieces having the slit positioned between the center line of the absorbent body and a second peripheral edge of the absorbent body;

a plurality of second bending element pieces, each second bending element piece extending for a second prescribed length that is substantially parallel with the second axis, and the plurality of second bending element pieces including:

i) second bending element pieces having the slit positioned to cross the center line of the absorbent body, (ii) second bending element pieces having the slit arranged to reach the second peripheral edge of the absorbent body, and (iii) second bending element pieces having the slit positioned between the center line of the absorbent body and the second peripheral edge of the absorbent body;

a third bending element piece having an extended slit and positioned near the center line of the absorbent body and extending toward the peripheral edges of the absorbent body from the second axis at a specified angle; and a covering material having a body side face facing a body side and an opposite side face facing away from the body side, the covering material enclosing the absorbent body while maintaining an effect of the bending elements, the covering material defining a main form of the interlabial pad, wherein a surface of the covering material is not provided with slits, wherein each of a plurality of first crossover points is formed from one of the plurality of first bending element pieces having the slit positioned along the center line and one of the plurality of second bending element pieces positioned to cross the center line, and each of a plurality of second crossover points is formed from one of the plurality of first bending element pieces having the slit positioned between the center line and the second peripheral edge and one of the plurality of second bending element pieces having the slit positioned between the center line of the absorbent body and the second peripheral edge of the absorbent body, and wherein the absorbent body is folded in two along the centerline being at the first crossover points to form a long protrusion part so that portions of the opposite side face are positioned to face each other and extension parts extend laterally from the long protrusion part at the second crossover points, and wherein the opposite side surface to a body of the interlabial pad comprises a mini sheet piece which is provided over one side part to another side part, wherein both side parts are substantially parallel to the first axis of the interlabial pad; and a finger insert hole is formed between the mini sheet piece and the opposite side surface to the body.

2. The interlabial pad according to claim 1, wherein each slit has a length of 3 to 30 mm and a breadth no greater than 5 mm, and a distance between each parallel adjacent slit is 3 to 20 mm.

3. The interlabial pad according to claim 1, wherein: the ones of the plurality of bending elements that are formed from each of a first bending element piece and a second bending element piece are arranged in a line that is symmetrical with respect to the center line of the interlabial pad, which lies along the first axis of the interlabial pad.

4. The interlabial pad according to claim 1, wherein each of the bending elements includes a low density portion.

5. The interlabial pad according to claim 1, wherein the interlabial pad is a pad for an incontinence of urine.

6. The interlabial pad according to claim 1, wherein the interlabial pad is a pad for absorbing vaginal discharge.

7. A method of adjusting a form flexibility used for an interlabial pad with a size, weight, flexibility capable of being held between labia by a part or the whole portion of the interlabial pad being naturally inserted therebetween, the interlabial pad having a first axis that is substantially parallel to an anteroposterior axis of a wearer, and a second axis which is included in a horizontal plane when the wearer is standing and is perpendicular to the first axis, the interlabial pad comprising:

an absorbent body for absorbing body fluid and a coating material for enclosing said absorbent body, the absorbent body defining a main form of the interlabial pad; and a plurality of bending elements each including a slit formed on a surface of the absorbent body with a prescribed length and a depth of approximately 3 to 5 mm and comprising at least one of pulp, chemical pulp, rayon, acetate, natural cotton, super absorbent polymer, fibrous super absorbent polymer, and synthetic fiber, the bending elements each being provided in a prescribed position of the absorbent body with a lower bending strength compared to positions of the absorbent body other than the prescribed position, in order to make the interlabial pad easy to bend into at least one of a U-shape or an S-shape, and a covering material having a body side face facing a body side and an opposite side face facing away from the body side, the covering material enclosing the absorbent body while maintaining an effect of the bending elements, the covering material defining a main form of the interlabial pad, wherein a surface of the covering material is not provided with slits, the opposite side surface to a body of the interlabial pad comprises a mini sheet piece which is provided over one side part to another side part, wherein both side parts are substantially parallel to the first axis of the interlabial pad; and a finger insert hole is formed between the mini sheet piece and the opposite side surface to the body;

wherein each of the plurality of bending elements is formed from a first bending element piece, a second bending element piece in which the slit is extended in both of the first bending element piece and the second bending element piece, and a third bending element having and extended slit and positioned near the center line of the absorbent body, wherein the first bending element piece extends in a substantially parallel direction to the first axis, the second bending element piece extends in a substantially parallel direction to the second axis, the third bending element extending toward the peripheral edges of the absorbent body from the second axis at a specified angle the first bending element piece and the second bending element piece for at least one of the plurality of bending elements cross each other near a center line substantially parallel to the first axis of the interlabial pad, and the first bending element piece and the second bending element piece for at least another one of the plurality of bending elements cross each other between the center line and a peripheral edge of the absorbent body, the method comprising the step of:

adjusting the form flexibility of the interlabial pad by a bending element application method using the plurality of bending elements.

8. The method of adjusting a form flexibility according to claim 7, wherein the adjustment method further comprises the step of changing one or more of the form, number, positioning area, and arrangement of one or more of the bending elements.

9. The interlabial pad according to claim 1, wherein the first bending element pieces having the slit positioned between the center line of the absorbent body and the first peripheral edge of the absorbent body are positioned at a boundary between an extension part of the interlabial pad and a long protrusion part of the interlabial pad.

\* \* \* \* \*